US012265406B2

(12) United States Patent
Winfield

(10) Patent No.: US 12,265,406 B2
(45) Date of Patent: Apr. 1, 2025

(54) COLLISION AVOIDANCE IN RADIOTHERAPY

(71) Applicant: Elekta Limited, Crawley (GB)

(72) Inventor: Colin Winfield, Crawley (GB)

(73) Assignee: Elekta Limited, Crawley (GB)

( * ) Notice: Subject to any disclaimer, the term of this patent is extended or adjusted under 35 U.S.C. 154(b) by 334 days.

(21) Appl. No.: 17/597,691

(22) PCT Filed: Jul. 16, 2020

(86) PCT No.: PCT/EP2020/070189
§ 371 (c)(1),
(2) Date: Jan. 18, 2022

(87) PCT Pub. No.: WO2021/013705
PCT Pub. Date: Jan. 28, 2021

(65) Prior Publication Data
US 2022/0261013 A1   Aug. 18, 2022

(30) Foreign Application Priority Data

Jul. 19, 2019 (GB) ..................... 1910381

(51) Int. Cl.
*G05D 3/20* (2006.01)
*A61B 34/10* (2016.01)
*A61N 5/10* (2006.01)

(52) U.S. Cl.
CPC .............. *G05D 3/20* (2013.01); *A61B 34/10* (2016.02); *A61N 5/1049* (2013.01); *A61N 5/107* (2013.01);
(Continued)

(58) Field of Classification Search
CPC ...... A61B 2034/2065; A61B 2034/105; A61B 2090/366; A61B 2090/373; A61B 34/20;
(Continued)

(56) References Cited

U.S. PATENT DOCUMENTS 5,727,554 A * 3/1998 Kalend ............... A61B 6/08
600/407
2004/0116804 A1 * 6/2004 Mostafavi ........... A61B 6/541
600/428

(Continued)

FOREIGN PATENT DOCUMENTS

EP 3406298 A1 11/2018
WO WO-2009011643 A1 1/2009

OTHER PUBLICATIONS

"International Application Serial No. PCT/EP2020/070189, International Search Report dated Sep. 30, 2020", (Sep. 30, 2020), 4 pgs.
(Continued)

*Primary Examiner* — Dani Fox
*Assistant Examiner* — Soorena Kefayati
(74) *Attorney, Agent, or Firm* — Schwegman Lundberg & Woessner, P.A.

(57) ABSTRACT

A method, apparatus and computer-readable medium for avoiding collisions between a subject and a radiotherapy device are provided. At a first time point, first location information for the subject is measured using a first sensor and a second sensor. A spatial profile of the subject is determined based on the first location information. At a second time point, second location information for the subject is measured using the first sensor. At this second time point, a line of sight between the second sensor and the subject is obscured. It is determined whether a collision is expected to occur between the subject and the radiotherapy device based on the spatial profile and the second location information.

18 Claims, 5 Drawing Sheets

(52) U.S. Cl.
CPC ... *A61B 2034/102* (2016.02); *A61B 2034/105* (2016.02); *A61N 2005/1059* (2013.01)

(58) Field of Classification Search
CPC .... A61B 90/37; A61N 5/1049; A61N 5/1048; A61N 5/1067; A61N 5/1069; A61N 2005/1059; A61N 2005/1061
See application file for complete search history.

(56) References Cited

U.S. PATENT DOCUMENTS

| | | | | |
|---|---|---|---|---|
| 2004/0257744 | A1* | 12/2004 | Bushko | A61B 6/102 361/179 |
| 2005/0281374 | A1* | 12/2005 | Cheng | B25J 9/1666 378/68 |
| 2010/0061509 | A1* | 3/2010 | D'Ambrosio | G01T 1/161 250/363.04 |
| 2010/0198112 | A1* | 8/2010 | Maad | A61B 6/541 600/595 |
| 2011/0249088 | A1* | 10/2011 | Hannibal | A61B 5/066 348/43 |
| 2012/0014501 | A1* | 1/2012 | Pelc | A61N 5/1049 378/9 |
| 2013/0289796 | A1* | 10/2013 | Bergfjord | A61N 5/1048 700/302 |
| 2014/0288348 | A1* | 9/2014 | Gross | A61N 5/1049 600/1 |
| 2015/0035942 | A1* | 2/2015 | Hampton | A61N 5/1049 348/42 |
| 2015/0159994 | A1* | 6/2015 | Hofmann | A61N 5/1049 356/623 |
| 2015/0209599 | A1* | 7/2015 | Schlosser | A61B 8/54 600/427 |
| 2016/0035108 | A1* | 2/2016 | Yu | A61B 5/721 382/131 |
| 2016/0074673 | A1* | 3/2016 | Allen | A61N 5/1049 600/1 |
| 2016/0166856 | A1* | 6/2016 | Popple | A61B 6/08 600/1 |
| 2017/0014648 | A1* | 1/2017 | Mostafavi | A61N 5/1081 |
| 2017/0136261 | A1* | 5/2017 | Hofmann | G01B 11/005 |
| 2017/0281975 | A1* | 10/2017 | Filiberti | A61N 5/1048 |
| 2019/0046132 | A1* | 2/2019 | Xu | A61B 6/5205 |
| 2019/0105514 | A1* | 4/2019 | Amstutz | A61B 34/20 |
| 2019/0143145 | A1* | 5/2019 | Laurence, Jr. | A61B 34/10 600/1 |
| 2019/0275351 | A1* | 9/2019 | Xu | A61N 5/1048 |
| 2019/0329073 | A1* | 10/2019 | Meltsner | A61N 5/1077 |
| 2020/0206536 | A1* | 7/2020 | Wang | A61N 5/1067 |
| 2020/0346036 | A1* | 11/2020 | Li | A61N 5/1039 |
| 2021/0196983 | A1* | 7/2021 | He | A61N 5/1048 |

OTHER PUBLICATIONS

"International Application Serial No. PCT/EP2020/070189, Written Opinion dated Sep. 30, 2020", (Sep. 30, 2020), 7 pgs.
"United Kingdom Application Serial No. 1910381.1, Examination Report dated Jan. 7, 2020", (Jan. 7, 2020), 6 pgs.
"European Application No. 20742710.5, Communication pursuant to Article 94(3) EPC dated Nov. 26, 2024", (Nov. 26, 2024), 5 pgs.

* cited by examiner

COLLISION AVOIDANCE IN RADIOTHERAPY

PRIORITY APPLICATIONS

This application is a U.S. National Stage Filing under 35 U.S.C. § 371 from International Application No. PCT/EP2020/070189, filed on Jul. 16, 2020, and published as WO2021/013705 on Jan. 28, 2021, which claims the benefit of priority to United Kingdom Application No. 1910381.1, filed on Jul. 19, 2019; the benefit of priority of each of which is hereby claimed herein, and which applications and publication are hereby incorporated herein by reference in their entireties.

This disclosure relates generally to radiotherapy, and in particular to collision avoidance in radiotherapy.

BACKGROUND

Radiotherapy uses ionising radiation to treat a human or animal body. In particular, radiotherapy is commonly used to treat tumours within a body. In such treatments, cells forming part of the tumour are irradiated by ionising radiation in order to destroy or damage them. However, in order to apply a prescribed dose of ionising radiation to a target location or a target region, such as a tumour, the ionising radiation will typically also pass through healthy tissue of the body.

Modern radiotherapy treatment uses techniques to reduce the radiation dose to healthy tissue and thereby provide a safe treatment. For example, one approach to minimising a radiation dose received by healthy tissue surrounding a target region is to direct the radiation towards the target region from a plurality of different angles, for example by rotating a source of radiation around the patient by use of a rotating gantry. In this case, the angles at which radiation is applied are selected such that each beam of radiation passes through the target region. In this way, a cumulative radiation dose may be built up at the target region over the course of a treatment delivery in which the radiation source rotates through a certain angle. However, since the radiation is applied from a plurality of different angles, the same, high, cumulative radiation dose is not built up in the healthy tissue because the specific healthy tissue the radiation passes through varies with angle. Therefore, a unit volume of the healthy tissue receives a reduced radiation dose relative to a unit volume of the target region.

However, the application of radiation from a plurality of different angles requires movement of a radiation source and/or movement of the patient, for example by movement of a patient support. In addition, since radiotherapy treatment may have a duration of the order of seconds or minutes, the patient may move relative to the patient support during the radiotherapy treatment. There are various reasons why a patient may move during or immediately prior to radiotherapy treatment. Gross or large-scale movement of a patient may include the patient shifting position or sitting up. Discrete movements of the patient may include the patient coughing or sneezing. In some cases, large-scale movements may correspond to discrete movements. The patient may also undergo cyclical, physiological movement such as breathing.

Due to geometrical and dosimetric considerations, it is often desirable for components of the radiotherapy device to be in close proximity to the patient. Due to this, and to the movements of the radiotherapy device and/or the patient, it is possible that a patient and a component of a radiotherapy device may collide during a radiotherapy treatment and/or that different components of the radiotherapy device may collide with each other. This may cause damage to the patient and/or the radiotherapy device. Such a collision may also cause a delay in the application of radiotherapy and/or inaccurate application of radiotherapy due to the associated disruption to the radiotherapy treatment.

In some prior approaches, touch guards are used to avoid a patient colliding directly with a component of a radiotherapy device. Such touch guards can be fitted over a component of a radiotherapy device such that a collision would occur between the patient and the touch guard instead of between the patient and the component of the radiotherapy device itself. However, such collisions can still cause damage to the patient, the touch guard and/or the radiotherapy device, particularly if the patient and/or a component of the radiotherapy device is moving at high speed. In addition, some components or accessories of a radiotherapy device may not be suitable for being covered by a touch guard.

In some prior approaches, one or more cameras may be used to monitor a position of a patient and/or equipment around the patient during a radiotherapy treatment. However, due to movement of components of the radiotherapy device and/or the patient, one or more of the camera views may become obscured during the radiotherapy treatment. Accordingly, the avoidance of collisions may not be as effective or as reliable as would be desired.

Regulators may limit the speed at which components of the radiotherapy device and/or the patient are allowed to move at in view of the risk of collisions occurring. This can prolong the duration of a radiotherapy treatment. It can also lead to a compounded risk of collisions occurring and inaccuracies in delivery of radiotherapy due to an increased chance of patient movement in longer time periods. In addition, such limitations can reduce patient throughput, limiting the efficient utilisation of a radiotherapy device.

It would be advantageous to improve collision avoidance in radiotherapy treatment in order to improve the safety and reliability of radiotherapy treatment. It would also be advantageous to increase patient throughput to provide improved efficiency of radiotherapy treatment.

The present invention seeks to address these and other disadvantages encountered in the prior art by providing improved collision avoidance in radiotherapy.

SUMMARY

An invention is set out in the claims.

According to an aspect, there is provided a method for avoiding a collision between a subject and a radiotherapy device, the method comprising: measuring, at a first time point, first location information for the subject using a first sensor and a second sensor; determining a spatial profile of the subject based on the first location information; measuring, at a second time point, second location information for the subject using the first sensor, wherein a line of sight between the second sensor and the subject at the second time point is obscured; and determining whether a collision is expected to occur between the subject and the radiotherapy device based on the spatial profile and the second location information.

According to a further aspect, there is provided an apparatus for use with a radiotherapy device, the apparatus comprising: a first sensor configured to measure first location information for a subject at a first time point; and a second sensor configured to measure first location information for the subject at the first time point, wherein the first sensor is further configured to measure second location information for the subject at a second time point at which a line of sight between the second sensor and the subject is obscured, the apparatus further comprising a controller configured to: determine a spatial profile of the subject based on the first location information; and determine whether a collision is expected to occur between the subject and the radiotherapy device based on the spatial profile and the second location information.

According to a further aspect, there is provided a computer readable medium comprising computer executable instructions which, when executed by a processor, cause the processor to perform any of the methods disclosed herein.

According to a further aspect, there is provided a radiotherapy device comprising any of the apparatus components disclosed herein.

FIGURES

Specific embodiments are now described, by way of example only, with reference to the drawings, in which.

DETAILED DESCRIPTION

In presently disclosed methods, improved means for avoiding a collision occurring in radiotherapy treatments are provided. When a view of a subject is obscured such that only partial location information for a subject is available, more complete location information measured before the view is obscured can be combined with the partial location information to determine whether a subject has moved and/or whether a collision is expected to occur. A spatial profile of a subject can be determined based on location information measured by a plurality of sensors. Obscuring of the line of sight between one or more of the plurality of sensors and the subject can be compensated for by extrapolating from the view of one of the sensors which does not have an obscured line of sight to the subject. The spatial profile and the view of this sensor can be used to determine if and to what extent the subject has moved and/or whether a collision between the subject and a radiotherapy device is expected. If a collision is expected to occur, treatment can be halted or adjusted in order to avoid the collision occurring.

In the following, a method, apparatus and computer-readable medium for avoiding a collision in radiotherapy are provided. The apparatus may be configured to perform any of the method steps presently disclosed and may comprise computer executable instructions which, when executed by a processor, cause a processor to perform any of the method steps presently disclosed. Any of the steps that the apparatus is configured to perform may be considered as method steps of the present disclosure and may be embodied in computer executable instructions for execution by a processor.

In the following, application of radiotherapy to a patient will be referred to in most detail in order to provide clarity of explanation. Such use of the term patient should not be interpreted to limit application of the present disclosure. The present disclosure provides means that can be used to apply radiotherapy to any subject. The terms patient and subject may be used interchangeably herein.

Figure 1A:
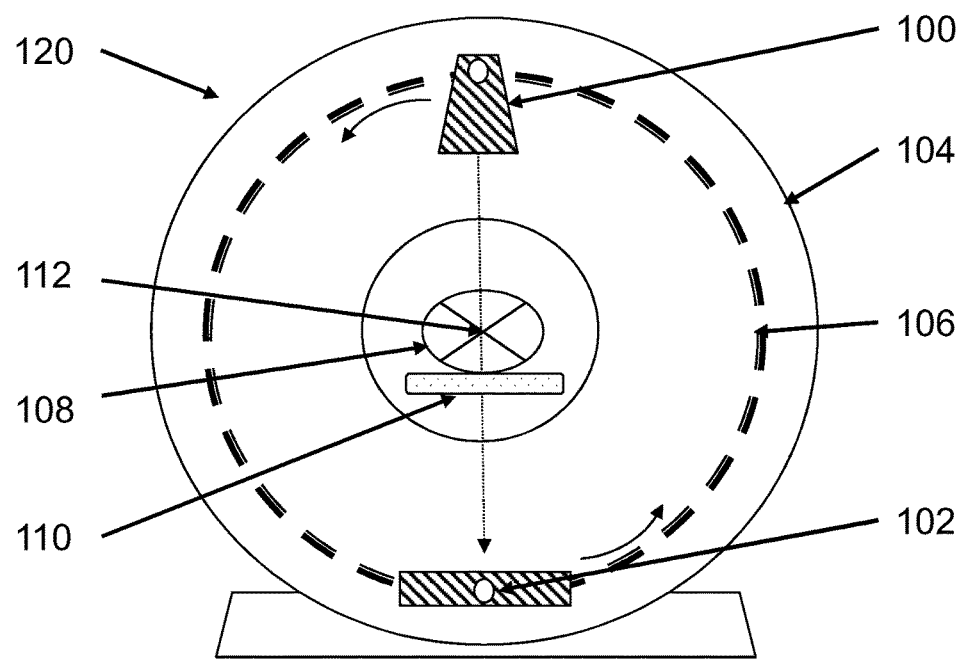
FIGS. 1a-1b depict a radiotherapy device according to the present disclosure.

FIG. 1a depicts a radiotherapy device according to the present disclosure. The arrangement described should be considered as providing one or more examples of a radiotherapy device 120 and it will be understood that other arrangements are possible and can be used to perform the methods described herein. The Figure shows a cross-section through a radiotherapy device 120 comprising a radiation source 100 and a detector 102 attached to a gantry 104. The radiation source 100 and the detector 102 may be fixed to the gantry 104 and may rotate with the gantry. The gantry 104 may comprise a circular support track 106. The radiation source 100 and the detector 102 may be arranged diametrically opposed to one another.

FIG. 1a also depicts a subject 108 on a support surface 110. The support surface 110 may be moved longitudinally relative to the gantry 104 (i.e. away from the plane of the gantry 104), for example to aid positioning of the subject 108. In some examples, the support surface 110 may be moved along other translational axes (e.g. in the plane of the gantry) and/or rotational axes. A controller may have access to position and/or movement information for the support surface 110 and may use this information for collision avoidance. As radiation is applied to the subject 108, for example according to a treatment plan, the radiation source 100 and the detector 102 may rotate together with the gantry 104 and/or around the circular support track 106 such that they are always arranged 180° from one another. The radiation source 100 may direct radiation towards the subject 108 from various angles around the subject 108 in order to spread out the radiation dose received by healthy tissue to a larger region of healthy tissue while building up a prescribed dose of radiation at a target region. As shown in FIG. 1a, radiation may be emitted in a plane which is perpendicular to the axis of rotation of the radiation source 100. Thus, radiation may be applied to a radiation isocentre 112 at the centre of the gantry 104 regardless of the angle to which the radiation source 100 is rotated around the gantry 104. The spatial distribution of the application of radiation may be adjusted using a collimator, for example a multi-leaf collimator, arranged in a path of a radiation beam emitted by the radiation source 100.

In some examples, the radiation source 100 and the detector 102 may be disposed in the plane of the gantry 104. In other examples, the radiation source 100 and the detector 102 (as well as other components of the radiotherapy device 120) may be projected from the gantry 104. In such examples, these components may be disposed at a certain longitudinal distance from the plane of gantry 104.

Figure 1B:
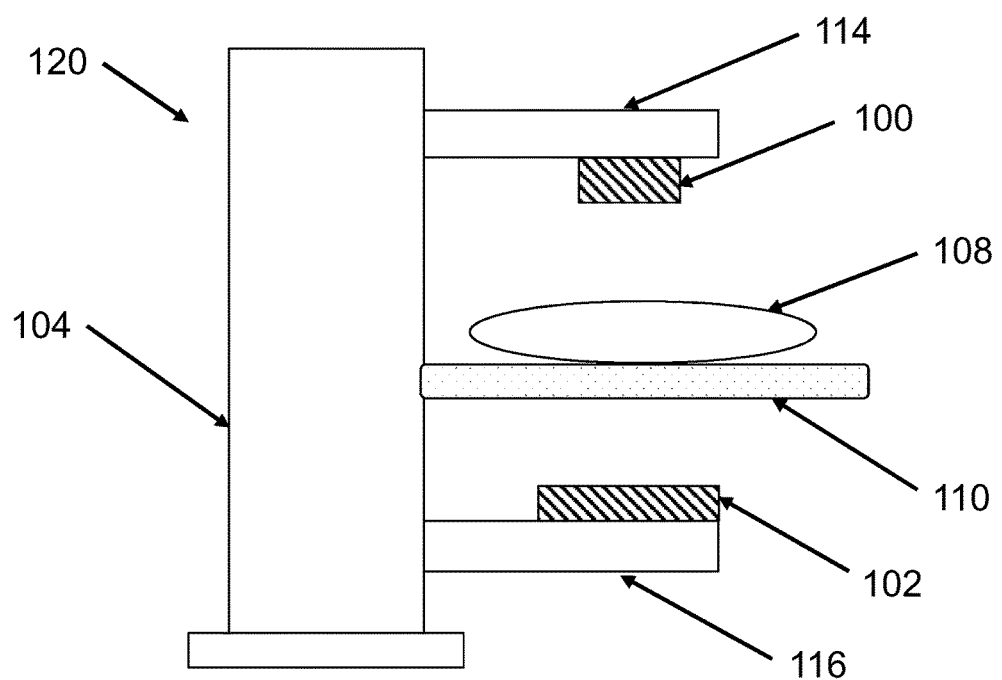

FIG. 1b depicts a further view of a radiotherapy device according to the present disclosure. While FIG. 1a may depict a radiotherapy device 120 from a longitudinal end of the radiotherapy device 120, FIG. 1b may depict a radiotherapy device 120 from a lateral side of the radiotherapy device 120. In other words, FIG. 1b may depict a side profile of the radiotherapy device 120. From the orientation depicted in FIG. 1a, FIG. 1a may depict the radiation source 100 and the detector 102 disposed in the plane of the gantry 104, or may depict these components being projected longitudinally from the gantry 104. However, FIG. 1b depicts a radiotherapy device 120 in which the radiation source 100 and the detector 102 are projected longitudinally from the gantry 104. In particular, the radiation source 100 may be disposed on a support arm 114, which may connect the radiation source 100 to the gantry 104. The detector 102 may be disposed on a support arm 116, which may connect the detector 102 to the gantry 104. The methods and apparatuses described in the present disclosure are applicable to each of the above-described configurations.

In some examples, the radiotherapy device 120 may comprise one or more additional panels and/or sources and/or detectors. The radiotherapy device 120 may comprise one or more imaging devices, which may comprise a source and a detector. This source and detector may be fixed to the gantry 104 and/or may rotate around the circular support track 106 such that they are always 180° from each other. This source and detector may be disposed in the plane of the gantry 104 or may be projected a longitudinal distance from the gantry 104, for example on additional support arms. In some examples, the radiotherapy device 120 may be an MR linac. As used herein, any of the above-described features may be referred to as components of the radiotherapy device. The radiotherapy device 120 may comprise a magnetic resonance (MR) imaging device, which may not comprise a detector separate from a source of the MR imaging device.

A treatment delivery may comprise rotation of the radiation source 100 and application of radiation by the radiation source 100, for example according to a treatment plan. In a treatment delivery, the rotation of the radiation source 100 may be through a predetermined angle. The radiation source 100 may rotate in a continuous or substantially continuous treatment arc, and/or may rotate to and pause at a plurality of discrete angles. The treatment plan comprises a prescribed dose (e.g. a clinically-prescribed dose) for the target region.

As described above, one or more components of the radiotherapy device 120 may move around a subject 108 on the gantry 104 and/or on the circular support track 106. Alternatively, or in addition, the support surface 110 may move relative to the gantry 104. These movements may occur prior to or during a radiotherapy treatment in order to direct a radiation beam towards the subject 108 from one or more particular angles. These angles may be determined based on a treatment plan, which may be based on a location/distribution of unhealthy tissue of the subject 108. Alternatively, or in addition, the subject 108 may move relative to the support surface 110, and therefore (in general) relative to the other components of the radiotherapy device.

Based on the above description of the various movements that can occur, it will be appreciated that there is a need for monitoring a location of the subject 108 and the components of the radiotherapy device 120 during a radiotherapy treatment, and thereby for providing means for avoiding collisions between the subject 108 and the components of the radiotherapy device 120.

Figure 2A:
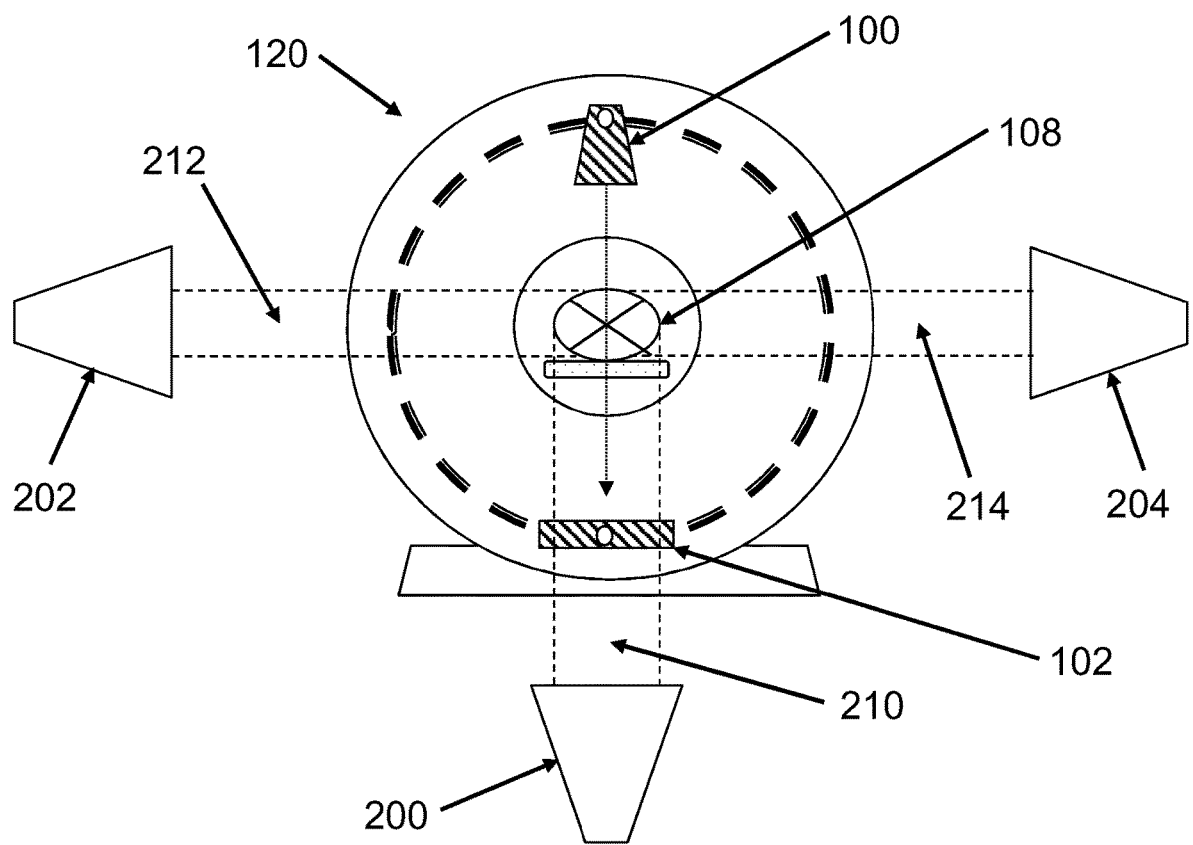
FIG. 2a depicts an arrangement of sensors and a radiotherapy device according to the present disclosure.

FIG. 2*a* depicts an arrangement of sensors and a radiotherapy device according to the present disclosure. The Figure depicts the sensors arranged around the radiotherapy device 120. The radiotherapy device 120 may correspond to the radiotherapy device 120 depicted in FIG. 1*a* and/or FIG. 1*b*. FIG. 2*a* may depict the radiotherapy device 120 at a first time point. The first time point may be prior to the start of a radiotherapy treatment or during a radiotherapy treatment. The sensors may include one or more sensors 200, 202, 204. For example, the sensors 200, 202, 204 may include an end sensor 200 and one or more side sensors 202, 204. It will be understood that some examples may include more or fewer sensors 200, 202, 204 than are depicted in FIG. 2*a* and that one or more sensors 200, 202, 204 may be positioned in different locations and/or with different orientations. In some examples, a plurality of sensors may be used. As used herein, each of the sensors 200, 202, 204 may be described as a first sensor, a second sensor or a third sensor. Each of the sensors 200, 202, 204 may include a plurality of sub-sensors. Such sub-sensors may be of different types. In other words, the sub-sensors may measure different physical quantities or may measure in different ranges of physical quantities (e.g. different wavelength ranges). Alternatively, or in addition, such sub-sensors may provide measurements from slightly different locations and/or may provide redundancy in case of errors or failure of a sub-sensor.

As depicted in FIG. 2*a*, the sensor 200 may have a line of sight 210 to the subject 108. The sensor 202 may have a line of sight 212 to the subject. The sensor 204 may have a line of sight 214 to the subject 108. As used herein, the term line of sight may be used interchangeably with the term view. These terms may be used to indicate a view of a subject 108 that is unobscured, for example completely unobscured or at least partially unobscured. For example, a sensor 200, 202, 204 may have a line of sight 210, 212, 214 to the subject 108 if at least a predetermined proportion of the subject 108 is viewable by the sensor 200, 202, 204, or if the subject 108 is viewable by the sensor 200, 202, 204 over at least a predetermined distance or angular range.

The end sensor 200 may be disposed approximately level with (i.e. at a same vertical height as) or higher than (i.e. at a higher vertical height than) the support surface 110 and/or the subject 108 and directed towards the support surface 110 and/or the subject 108. In other words, the end sensor may be disposed along a central axis of the radiotherapy device 120 (e.g. the gantry 104 of the radiotherapy device 120) and may be directed towards the radiotherapy device 120. Thus, while when viewed in the plane depicted in FIG. 2*a* it may appear that the line of sight 210 is obscured by the detector 102, since the end sensor 200 may be disposed level with or higher than the support surface 110 and/or the subject 108, the line of sight 210 should not be considered to be obscured by the detector 102. In other words, when viewed from the orientation of FIG. 1*b*, the end sensor 120 may be disposed on the right side of FIG. 1*b*. The end sensor 120 may be disposed at approximately the same height as the subject 108 or the support surface 110 or may be disposed at a lower or higher vertical height than the support surface 110 or the subject 108 so as to provide an upward or downward view of the subject 108 respectively. Preferably, the end sensor 120 is disposed at a higher height than the support surface 110 in order to provide an improved view of the subject 108 and/or the support surface 110.

The side sensors 202, 204 may be disposed at sides of the radiotherapy device 120. For example, the side sensor 202 may be disposed on the left side of the radiotherapy device 120, when viewed from the orientation depicted in FIG. 2*a*. Similarly, the side sensor 204 may be disposed on the right side of the radiotherapy device 120, when viewed from the orientation depicted in FIG. 2*a*. Each of the side sensors 202, 204 may be directed towards the subject 108. The side sensors may be disposed level with (i.e. at a same vertical height as) the support surface 110 and/or the subject 108, or may be disposed at a lower or higher vertical height than the support surface 110 and/or the subject 108 so as to provide an upward or downward view of the subject respectively. In some examples, the side sensors 202, 204 may be disposed approximately half way along the length of the support surface 110 and/or the subject 108. The side sensors 202,

204 may be disposed laterally relative to the radiotherapy device (e.g. may be disposed in a plane of the gantry 104) and directed towards the radiotherapy device. The focal point of the side sensors 202, 204 may coincide with the radiation isocentre 112 of the radiotherapy device 120.

The side sensors 202, 204 may be disposed in a same plane as the source 100 and the detector 102. This may be the case in examples in which the radiation source 100 and the detector 102 are projected longitudinally from the gantry 104, for example on support arms. In examples in which the radiation source 100 and the detector 102 are disposed in the same plane as the gantry 104, the side sensors 202, 204 may be disposed at a certain longitudinal distance from the gantry 104. In such examples, the side sensors 202, 204 may only have unobscured lines of sight 212, 214 to the subject 108 when the support surface 110 is withdrawn from (i.e. not inserted into) a bore of the gantry 104. In these examples, the first time point may be prior to the beginning of a radiotherapy treatment. In these examples, at the second time point, i.e. during the radiotherapy treatment, the views of the side sensors 202, 204 may always be obscured.

In some examples, the side sensors 202, 204 may be fixed to the ceiling or the walls of a room in which the radiotherapy device 120 is disposed. In other examples, the side sensors 202, 204 may be free-standing and/or fixed to the radiotherapy device 120 and/or fixed to supports.

In some examples, one or more of the sensors 200, 202, 204 may be a camera. Such a camera may be configured to take measurements in the visible wavelength range and/or in the infra-red wavelength range. Alternatively, or in addition, one or more of the sensors 200, 202, 204 may be LIDAR sensors, which may measure distances to parts of the subject 208 by illuminating the target with pulsed laser light and measuring the reflected pulses of light with a sensor. Alternatively, or in addition, any other imaging or distance measuring means known in the art may be used.

Figure 2B:
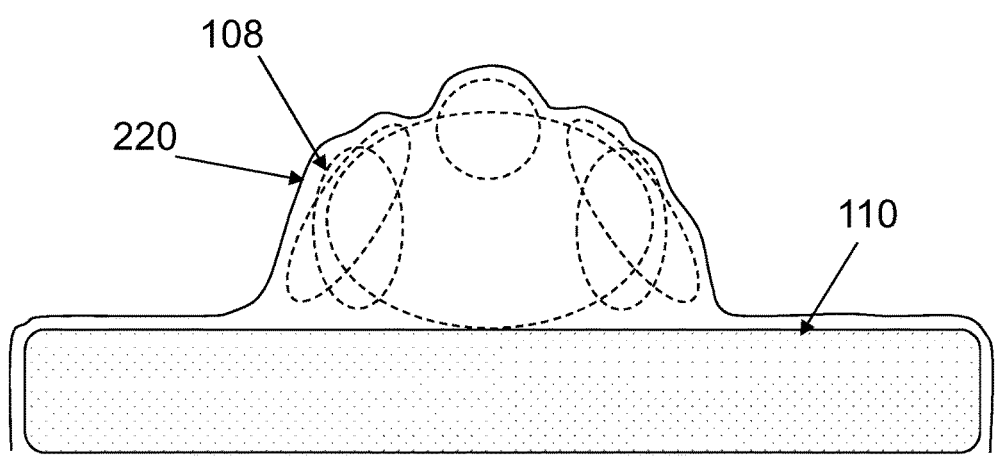
FIGS. 2b-2d depict profiles of a subject according to the present disclosure.

FIG. 2b depicts a profile of a subject according to the present disclosure. The Figure may depict a subject 108 at the first time point, corresponding to the arrangement shown in FIG. 2a. In FIG. 2b, the subject 108 (depicted using dashed lines) is depicted as being reclined on the support surface 110. It will be understood that other arrangements of the subject 108 are possible. The view depicted in FIG. 2b may be a view from the sensor 200, i.e. it may depict an end profile. The sensor 200 may view a most-extended profile 220 of the subject 108. In other words, the sensor 200 may be used to determine the points of maximum extension of the subject 108 from the support surface 110. The most-extended profile 220 may include a buffer or margin determined by the controller, for example based on uncertainties in the location of the patient and/or based on movements of the patient below a threshold distance.

Figure 2C:
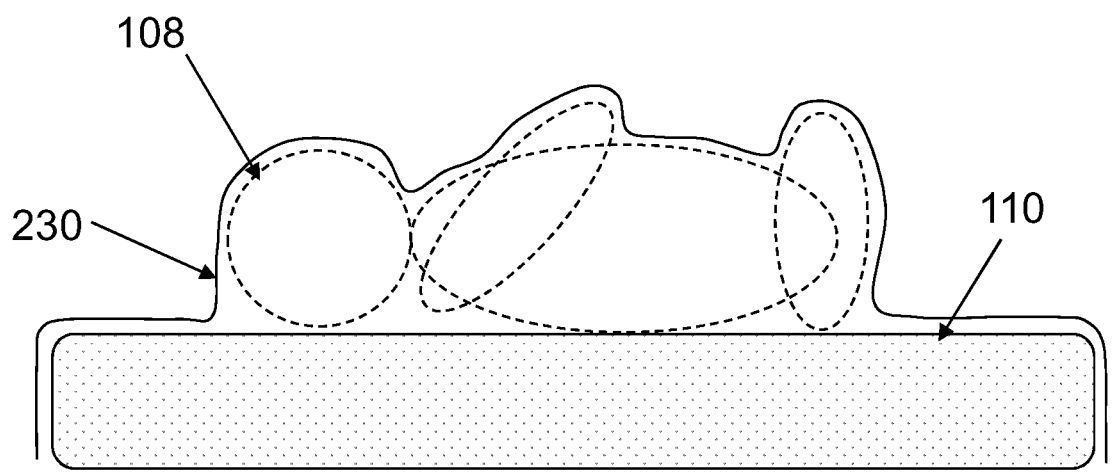

FIG. 2c depicts a profile of a subject 108 according to the present disclosure. The Figure may depict a subject 108 at the first time point, corresponding to the arrangement shown in FIGS. 2a and 2b. In FIG. 2c, the position of the subject 108 (depicted using dashed lines) may correspond to that shown in FIG. 2b. The view depicted in FIG. 2c may be a view from the sensor 202, i.e. it may depict a side profile. The sensor 202 may view a most-extended profile 230 of the subject 108. In other words, the sensor 202 may be used to determine the points of maximum extension of the subject 108 from the support surface 110.

Figure 2D:
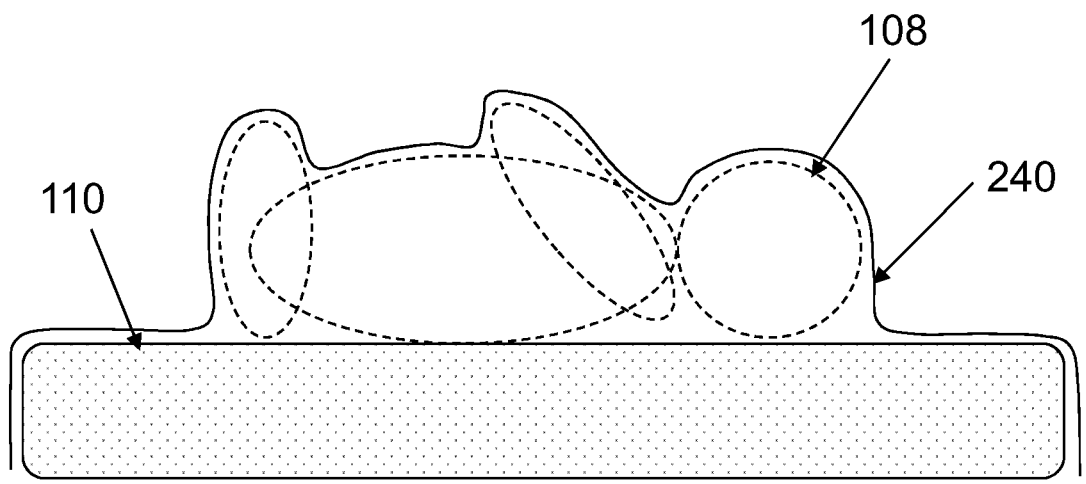

FIG. 2d depicts a profile of a subject according to the present disclosure. The Figure may depict a subject 108 at the first time point, corresponding to the arrangement shown in FIGS. 2a, 2b and 2c. In FIG. 2d, the position of the subject 108 (depicted using dashed lines) may correspond to that shown in FIGS. 2b and 2c. The view depicted in FIG. 2d may be a view from the sensor 204, i.e. it may depict a side profile. The sensor 204 may view a most-extended profile 240 of the subject 108. In other words, the sensor 204 may be used to determine the points of maximum extension of the subject 108 from the support surface 110.

As will be appreciated, the most-extended profile 240 may correspond to the most-extended profile 230, but may be from the opposite side of the subject 108. This is represented in FIG. 2d by the orientation depicted being opposite to that depicted in FIG. 2c. The subject may be approximately symmetrical longitudinally. One of the sensors 202, 204 may not be required/used, and a symmetry of the subject may be used to extrapolate from the most-extended profile 230 to the most-extended profile 240 (or vice versa).

The most-extended profiles 220, 230, 240 may provide location information for the patient from different orientations. The location information may be geometric information comprising position information and/or shape information. As used herein, where first and second sensors are described as measuring location information, this may be taken to indicate that the first sensor measures a first part of the first location information and the second sensor measures a second part of the first location information. The first part of the first location information and the second part of the first location information may be described collectively as the first location information. The first part of the first location information may overlap at least partly with the second part of the first location information. A spatial profile of the subject 108 may be determined based on the most-extended profiles 220, 230, 240. The spatial profile may be three-dimensional, for example a volume contour. This is enabled through the most-extended profiles 220, 230, 240 being obtained from different orientations. These measurements can be combined to provide three-dimensional information. This may be calculated based at least in part on known positions and orientations of the sensors 200, 202, 204 relative to the radiotherapy device 120. The spatial profile may comprise a body contour for a patient. In some examples, the body contour may also include parts of patient-positioning devices such as the support surface 110. In some examples, the spatial profile may be compared to a reference spatial profile to determine whether the subject 108 is in an intended treatment position. This can help to achieve accurate patient setup. In some examples, the intended treatment position can be derived and/or adjusted based on whether a collision is expected to occur during a radiotherapy treatment based on a known treatment plan.

In some examples, the spatial profile may be determined using only the most-extended profiles 220 and 230 or using only the most-extended profiles 220 and 240. The spatial profile may be determined using a controller communicatively coupled to the sensors. The spatial profile may comprise a location and/or position of the subject 108 at the first time point. For example, the spatial profile may be determined based on location information measured before radiotherapy treatment has commenced. Alternatively, the spatial profile may be determined based on location information measured during the radiotherapy treatment.

The controller may be communicatively coupled to one or more of the sensors 200, 202, 204 and/or to one or more components of the radiotherapy device 120. The controller may comprise, or be described as, a computing device or a processor. The controller may be configured to receive location information for the subject 108 and/or for components of the radiotherapy device 120. The controller may be any machine capable of executing a set of instructions (sequential or otherwise) that specify actions to be taken by the radiotherapy device and the components thereof as described herein. In some examples, the controller may comprise part of the radiotherapy device 120. In other examples, the controller may be disposed and/or operated in a device that is functionally and/or physically separate to the radiotherapy device 120.

Figure 3A:
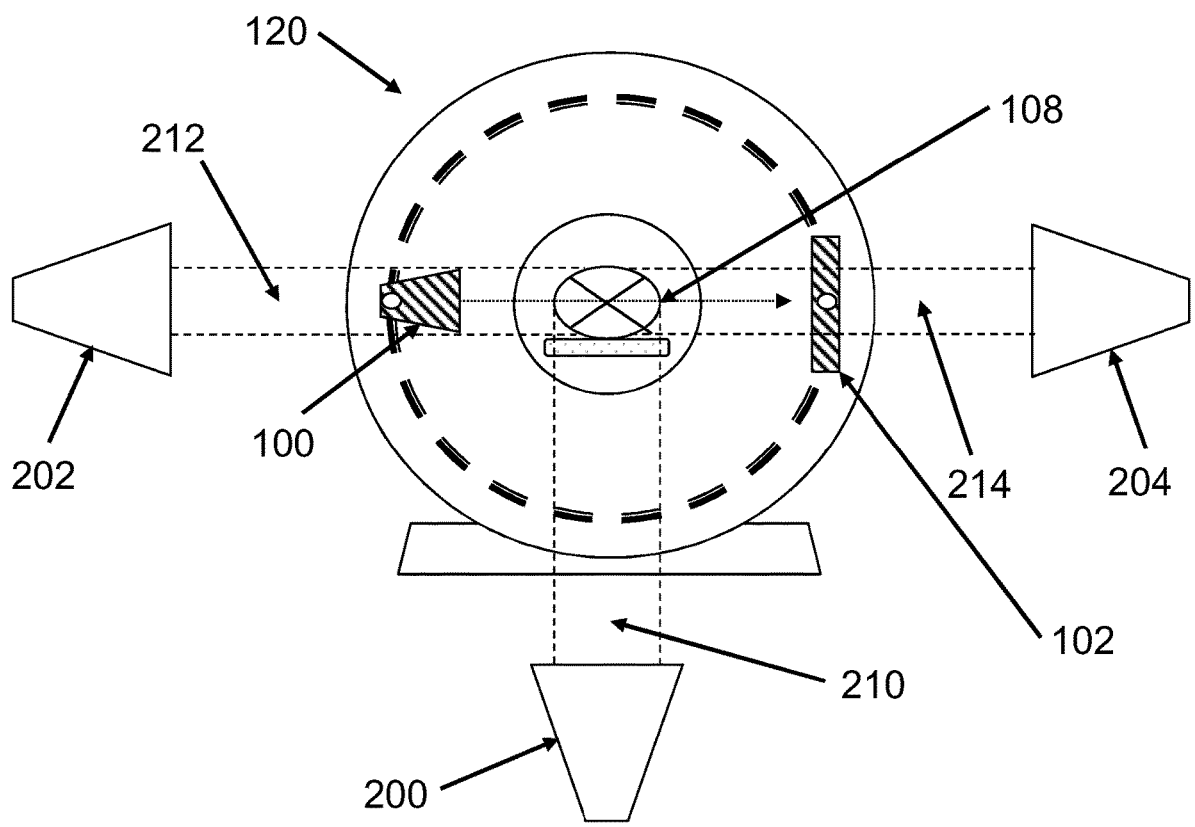
FIG. 3a depicts an arrangement of sensors and a radiotherapy device according to the present disclosure.

FIG. 3a depicts an arrangement of sensors and a radiotherapy device according to the present disclosure. The sensors 200, 202, 204 and the radiotherapy device 120 depicted in FIG. 3a may correspond to these elements as depicted in FIG. 2a. FIG. 3a may depict these elements at a second time point, which may be at a time after the first time point. For example, the second time point may be during a radiotherapy treatment and/or at a later time during the radiotherapy treatment than the first time point.

As depicted in FIG. 3a, at the second time point, the source 100 and the detector 102 may have rotated around the gantry 104 and/or the circular support track 106. Accordingly, the line of sight 212 of the side sensor 202 may be blocked by the radiation source 100. The line of sight 214 of the side sensor 204 may be blocked by the detector 102. In other examples, depending on the angle of rotation of the source 100 and the detector 102, the line of sight 212 of the side sensor 202 may be blocked by the detector 102 and/or the line of sight 214 of the side sensor 204 may be blocked by the radiation source 100. In other examples, the line of sight 212, 214 of one or more of the side sensors 202, 204 may be obscured by other components of the radiotherapy device 120, for example a source and/or a detector of an imaging device. Such imaging devices may include an X-ray imager, comprising a source and a detector on either side of the subject 108, and/or an MR imager, comprising a magnet and a detecting coil. The X-ray imager may comprise an MV imager, comprising a source corresponding to the radiation source 100 in a treatment beam head and an MV panel on an opposite side of the subject 108 at 180° to the treatment beam head. The kV X-ray imager may comprise a kV imager, comprising a kV radiation source at a fixed relative position to the treatment beam head and a kV detector on an opposite side of the subject 108 to the kV radiation source. In some arrangements, only one of the sensors 202, 204 may be blocked/obscured. For example, the sensor 202 and the sensor 204 may be positioned at different levels (i.e. different vertical heights) such that the line of sight 212, 214 of only one of the sensors 202 and 204 is blocked/obscured, the source 100 and the detector 102 being 180° apart. In some examples in which the radiation source 100 and the detector 102 are in the same plane as the gantry 104, the line of sight 212 and/or the line of sight 214 may be blocked/obscured by the gantry 104 at the second time point.

In the arrangement shown in FIG. 3a, one or both of the lines of sight 212, 214 of the sensors 202, 204 may be obscured. In other words, the sensor 202 and/or the sensor 204 may not have a view of the subject 108. As will be appreciated, this may make avoiding collisions between the subject 108 and the radiotherapy device 120 more difficult and/or less reliable. For example, movement of the subject 108 may not be identified by the sensors 202, 204, or may not be identified as accurately as would be desired.

Figure 3B:
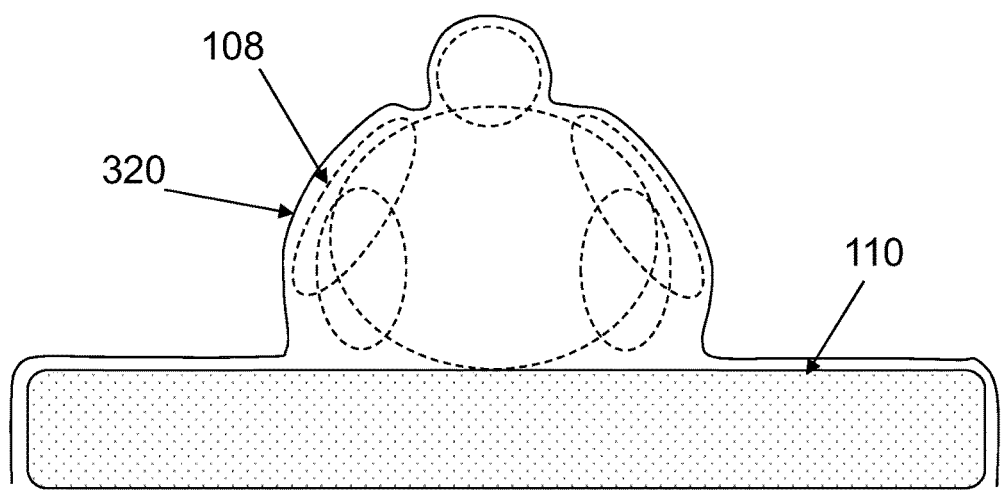
FIG. 3b depicts a profile of a subject according to the present disclosure.

FIG. 3b depicts a profile of a subject 108 according to the present disclosure. It may depict the subject 108 at the second time point, corresponding to the arrangement shown in FIG. 3a. The depiction of the subject 108 in FIG. 3b may be similar to the depiction of the subject in FIG. 3a.

However, in FIG. 3b, the subject 108 (depicted using dashed lines) may have moved relative to the location/position of the subject 108 depicted in FIG. 2b (and FIGS. 2c and 2d). In the example shown in FIG. 3b, the subject 108 may have moved to a sitting position, or between a reclined position and sitting position. It will be appreciated that other movements are within the present disclosure, for example a movement of a limb or a head of a patient.

The sensor 200 may view a most-extended profile 320 of the subject 108. Even in examples in which the radiation source 100 and the detector 102 are disposed in a same plane as the gantry 104, the sensor 200 may still measure location information for the subject 108 (i.e. the most-extended profile 320 may be determined) based on the line of sight 210 along a longitudinal axis of the radiotherapy device 120 (e.g. down a bore of the radiotherapy device 120).

In some examples, an imaging system may be fixed to the support surface 110 and may rotate around the subject 108 to acquire a 3-D image. In such examples, one or more components of the imaging system and/or the support structure thereof may obscure lines of sight 212, 214 of one or more of the sensors 202, 204. However, the line of sight 210 of the end sensor 200 may not be obscured by the imaging system or the support structure thereof.

In some examples, the movement of the subject 108 may reduce a volume of the most-extended profile 320 of the subject. If the most-extended profile 320 is within the previous most-extended profile 220 at all points (or at least at a specified sub-set of the points), the controller may determine that no collision is expected and may not continue with further analysis. This may reduce unnecessary processing and increase an efficiency of the controller.

At the second time point, views corresponding to those of FIG. 2c and/or FIG. 2d may not be available due to one or both of the lines of sight 212, 214 being obscured. Therefore, it may not be possible to determine the position of the subject 108 as accurately as desired.

For example, it may not be possible to accurately determine the position/location of the subject 108 in three dimensions using only the most-extended profile 320. However, the spatial profile determined for the position/location of the subject 108 at the first time point may be used together with the most-extended profile 320 to determine a movement of the subject 108. The movement of the subject 108 may comprise a part of the subject 108 that has moved, a distance the subject 108 or part of the subject 108 has moved and/or a change in orientation or shape of the subject 108 or part of the subject 108. It may not be possible to determine this three-dimensional information using a two-dimensional view alone. For example, depending on the position of the subject 108, it may not be possible to accurately determine the position/location of the subject in three dimensions based on the line of sight 210 from the sensor 200 alone. However, by combining the spatial profile at the first time point with the line of sight 210 from the sensor 200 at the second time point, the movement may be determined more accurately. This can enable the movement/location of the subject 108, and an expected collision, to be determined in three-dimensions even when one or both of the sensors 202, 204 have obscured lines of sight 212, 214.

One or more of the most-extended profiles 220, 230, 240, 320 as presently disclosed may comprise a most-extended profile of the subject 108 and may or may not additionally comprise a most-extended profile of the support surface 110. Where the most-extended profile(s) 220, 230, 240, 320 do not additionally comprise a most-extended profile of the support surface 110, location information for the support surface 110 may be available, for example to the controller, as part of dimensions and positions of the components of the radiotherapy device 120 that are known/input to the controller.

Based on the movement of the subject 108, it may be determined whether a collision is expected to occur between the subject 108 and the radiotherapy device 120. A radiotherapy treatment may be adjusted in response to a determination that a collision is expected to occur between the subject 108 and the radiotherapy device 120. In some examples, the radiotherapy treatment may be halted. In other words, movement of one or more components of the radiotherapy device 120 may be halted. If the support surface 110 is in motion, this halting includes halting movement of the support surface 110. In other examples, the rotation of one or more components such as the source 100 and/or the detector 102 may be slowed down, sped up, or otherwise changed. In this manner, a collision may be avoided, but the radiotherapy treatment may be continued according to an updated treatment plan. For example, a rate of rotation and a dose rate of the radiation source 100 may be decreased. This may provide more time to react to an expected collision, for example by providing more time for repositioning of the subject 108 and/or for further adaptation of the treatment plan. Moreover, slowing a rate of rotation or translation means that applying a same braking force can cause movement to be stopped in a shorter distance (i.e. a stopping distance is reduced), thereby minimising any potential collision damage.

While the explanation above has described collisions between the subject 108 and the radiotherapy device 120, expected collisions with other components may also be determined using the methods of the present disclosure. For example, it may be determined whether a subject 108 is expected to collide with another component in a room in which radiotherapy treatment is being performed, for example a table or a wheelchair.

The dimensions of a radiotherapy device 120, and the dimensions of individual components of the radiotherapy device 120, may be known, for example from part specifications. In some examples, one or more representations or identifiers on the components may be configured to provide information or links to information giving the dimensions of the components. Any appropriate representation or identifier may be used, for example barcodes, RFID tags, QR codes etc. These may be readable by a corresponding reader, such as a barcode reader, an RFID tracker or a camera communicatively coupled to a computer program arranged to extract information or links from the representations or identifiers. This may enable the reader to retrieve dimension information for a particular radiotherapy device 120. Physical characteristics of the subject 108 may be determined in advance of radiotherapy treatment. For example, a spatial profile of the subject 108 may be determined. Alternatively, or in addition, height, mass, and/or fat content of the subject 108 may be measured. The information on the radiotherapy device 120 and the information on the subject 108 may be used to generate a three-dimensional model or simulation of the radiotherapy device 120 and the subject 108. A treatment plan, or information therefrom, may also be fed into the model. For example, the treatment plan may provide information on a planned movement of the subject 108 (on the support surface 110) and/or of components of the radiotherapy device 120. For example, the treatment plan may comprise predetermined, time-varying locations/angles of the source 100 and the detector 102.

Using the above-mentioned information, the model may determine whether any part of the subject 108 is expected to collide with any part of the radiotherapy device 120 during a planned radiotherapy treatment. If a collision is expected to occur, the treatment plan and/or the location of the subject 108 and/or of the radiotherapy device 120 may be adjusted. The model may be re-run until no collisions are expected to occur. If no collisions are expected to occur, the radiotherapy treatment may begin.

The model and the techniques discussed herein may also be used to avoid collisions between a first component of the radiotherapy device 120 and a second component of the radiotherapy device 120. For example, these can be used to avoid collisions between a first component of the radiotherapy device 120 and the support surface 110. Since the model may include positions and velocities of various components as a function of time, this can enable more accurate collision avoidance to be achieved and thereby can enable safer operation of a radiotherapy device.

In some examples, adaptive radiotherapy (ART) may be employed. In such examples, the treatment plan may be updated during the radiotherapy treatment, for example based on measurements by the sensors 200, 202, 204 and/or based on MR imaging. As described above, the treatment plan may also be updated based on a determination that a collision is expected to occur.

As explained above, the sensors 200, 202, 204 may be used to measure real-time location information for the subject 108 and/or components of the radiotherapy device 120. This real-time information can be fed into the model to provide real-time collision avoidance modelling, as well as pre-treatment collision avoidance modelling. For example, while it may be the case that no collision is expected to occur based on an initial position/location of a subject 108, this may no longer be the case following a movement of the subject 108. The model may be rerun constantly or at intervals or at pre-determined points of a radiotherapy treatment to iteratively determine using real-time information whether a collision is expected to occur.

As explained above, the present disclosure enables accurate determination of a three-dimensional spatial profile of a subject 108 even when lines of sight 212, 214 of sensors 202, 204 are obscured. Without this additional accuracy, in three dimensions, a subject 108 could collide with a part of a radiotherapy device 120. Alternatively, using prior approaches, it could be determined that a movement of a subject 108 has occurred, but it might not be possible to determine updated location information for the subject 108 in three dimensions or with adequate accuracy. This may cause a radiotherapy treatment to be halted based on an over-cautious approach. In other words, the particular movement of the subject 108 may not be such as to result in a collision. However, it may not be possible to determine this without the methods of the present disclosure and a radiotherapy treatment may be halted unnecessarily. However, using the methods of the present disclosure, a movement that is expected to cause a collision can be more accurately distinguished from a movement that is not expected to cause a collision. This greater accuracy can provide safer and more efficient radiotherapy treatment. Where a movement is determined that is not expected to cause a collision, one or more components of the radiotherapy device 120 may be adjusted to ensure that an intended radiation dose profile is applied at intended locations within the subject 108. This may involve updating the treatment plan.

The present disclosure also provides methods for using measurements of an obscured sensor 202, 204. For example, if the line of sight 214 of the sensor 204 is obscured by the detector 102, the sensor 204 may not have a view of the subject 108. However, this does not entail that measurements of the sensor 204 cannot provide useful information. For example, the fact that the line of sight 214 is obscured may provide location information for the detector 102 itself (or the source 100, or another component of the radiotherapy device 120). The sensor 204 may provide a measurement of the distance between the sensor 204 and the back of the detector 102. The dimensions (e.g. the thickness) of the detector 102 may be known and included in the model. Given the location of the back of the detector 102, and the thickness of the detector 102, a location of the front of the detector 102 can be determined. This information can be fed into the model for further determining whether a collision is expected to occur (e.g. between the subject 108 and the front of the detector 102).

Figure 4:
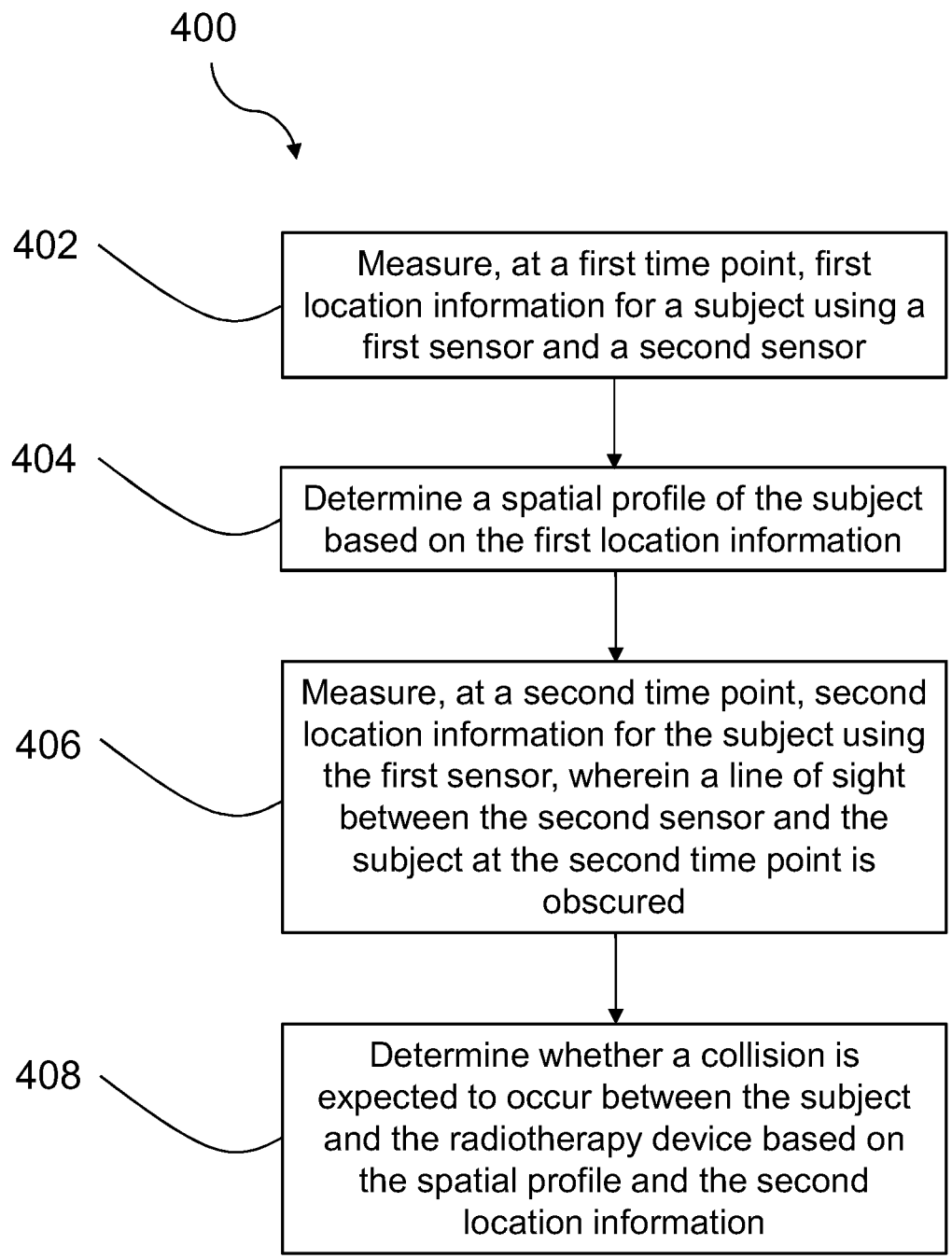
FIG. 4 depicts a method for avoiding a collision between a subject and a radiotherapy device according to the present disclosure.

FIG. 4 depicts a method for avoiding collisions between a subject and a radiotherapy device according to the present disclosure. The method 400 may be performed using the apparatus described herein, for example one or more of the sensors 200, 202, 204 and/or the controller.

In a step 402, at a first time point, first location information may be measured for the subject 108 using a first sensor 200 and a second sensor 202, 204. A first part of the first location information may be measured by the first sensor 200. A second part of the first location information may be measured by the second sensor 202, 204. The first part of the first location information may provide location information from a different viewpoint to the viewpoint of the second part of the first location information. The first location information may be a combination of location information measured by the first sensor 200 and the second sensor 202, 204, i.e. a combination of the first part of the first location information and the second part of the first location information. As used herein, references to location information for the subject 108 may refer to locations, shapes, positions and/or orientations of the subject 108 and/or parts of the subject 108.

In a step 404, a spatial profile of the subject 108 may be determined based on the first location information. The spatial profile may comprise a surface contour of the subject 108, for example a three-dimensional surface contour. This may be enabled by the first location information comprising measurements from the first sensor 200 and the second sensor 202, 204. In other words, the first sensor 200 and the second sensor 202, 204 may provide different viewpoints due to the different locations of the first sensor 200 and the second sensor 202, 204 relative to the subject 108. The spatial profile may be determined using a controller, which may analyse, process and/or combine the measurements of the first sensor 200 and the second sensor 202, 204.

In a step 406, at a second time point, second location information for the subject may be measured using the first sensor 200. At the second time point, a line of sight 212, 214 between the second sensor 202, 204 and the subject 108 may be obscured, for example by a component of the radiotherapy device 120. Therefore, measurement of second location information by the second sensor 202, 204 may not be possible at the second time point. The second time point may occur after the first time point, for example at a (later) time in a radiotherapy treatment at which one or more components of the radiotherapy device 120 may have moved relative to the first time point.

In a step 408, it may be determined whether a collision is expected to occur between the subject 108 and the radiotherapy device 120 based on the spatial profile and the second location information. The determination may be made by the controller. The controller may comprise a three-dimensional model of the radiotherapy device 120, which may provide the dimensions and/or locations of the radiotherapy device 120, which may vary with time according to a treatment plan. The controller may comprise or have access to the treatment plan, which may provide planned movements of components of the radiotherapy device 120 and/or the subject 108 during a radiotherapy treatment.

The determination may comprise determining whether (and to what extent) a movement of the subject 108 has occurred based on the spatial profile and the second location information. It may not be possible to determine this three-dimensional information using only a two-dimensional view alone. For example, depending on the positioning of the subject 108, it may not be possible to accurately determine the position/location of the subject 108 in three dimensions based on the line of sight 210 from the sensor 200 alone. However, the spatial profile at the first time point may provide three-dimensional spatial information for the subject 108. This may be combined with the line of sight 210 from the sensor 200 at the second time point in order to determine a movement of the subject. This can enable the movement to be determined accurately in three-dimensions even when one or both of the sensors 202, 204 have obscured lines of sight 212, 214. The determined movement of the subject 108 may be used to determine whether a collision is expected to occur between the subject 108 and the radiotherapy device 120. In other examples, the determination of a collision may be determined directly based on the spatial information and the second location information.

The determination may be performed by the controller, which may use one or more processing algorithms. For example, the controller may generate a model for the subject 108. The model may incorporate the spatial profile of the subject 108, which may provide information on the exterior surface of the subject 108, for example the dimensions of the subject 108. The model may comprise ranges of movement for the subject 108 or parts of the subject 108, which may be predetermined and/or based on standard ranges. For example, a possible range of movement of a limb relative to the rest of the subject 108 may be defined in the model. In another example, a possible range of movement of an upper body or spine of the subject 108 relative to the pelvis of the subject 108 may be defined in the model. In another example, a possible range of movement of a head of the subject 108 relative to the rest of the subject 108 may be defined in the model. It will be appreciated that other ranges of possible movements can be defined in the model. These ranges may be used to more accurately determine a movement of the subject and/or whether a collision is expected to occur based on the spatial profile and the second location information.

Based on the location of the subject 108 at the first time point, a collision between the subject 108 and the radiotherapy device 120 may not be expected. However, the controller may determine whether an altered location of the subject 108, due to a movement, results in a collision between the subject 108 and the radiotherapy device 120 being expected.

In response to a determination that the collision is expected to occur, the radiotherapy treatment may be halted or adjusted. For example, motion of one or more components of the radiotherapy device 120 may be halted or prevented. Alternatively, or in addition, motion of one or more components of the radiotherapy device 120 may be changed to follow a different angle and/or to proceed at a different speed. In response to a determination that a collision is not expected to occur, the radiotherapy treatment may be continued. However, if it is determined that the subject 108 has moved, motion of one or more components of the radiotherapy device 120 may still be changed to comprise a different angle and/or a different speed in order to ensure that an intended radiation dose profile is applied to an intended location within the subject 108.

As will be appreciated, further measurements may be taken at third and subsequent time points. Further determinations may be made using these measurements at the third and subsequent time points. These determinations may be performed in a similar manner to that described above in reference to the first time point and/or the second time point.

The method shown in FIG. 4 may be repeated during a radiotherapy treatment. For example, at a third time point the line of sight 212, 214 of the second sensor 202, 204 may not be obscured due to further movement of a component of the radiotherapy device 120. An updated spatial profile may be determined based on location information measured by the first sensor 200 and the second sensor 202, 204 at the third time point. This updated spatial profile may be used in place of the spatial profile in subsequent determinations of movement of the subject 108 and/or of expected collisions.

While the methods disclosed herein are presented in a certain sequential order, this should not be taken to limit the methods to the orders presented. One or more of the method steps may be omitted or rearranged. The various steps may be performed in different orders. Various steps may be performed at the same time or substantially the same time. Herein, references to events occurring substantially at the same time may refer to events at least partially overlapping in time and/or events occurring at the same time within measurement uncertainties.

The approaches described herein may be embodied on a computer-readable medium, which may be a non-transitory computer-readable medium. The computer-readable medium may carry computer-readable instructions arranged for execution upon a processor so as to cause the processor to carry out any or all of the methods described herein.

The term "computer-readable medium" as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

CLAUSES

1. A method for avoiding a collision between a subject and a radiotherapy device, the method comprising:
   measuring, at a first time point, first location information for the subject using a first sensor and a second sensor;
   determining a spatial profile of the subject based on the first location information;
   measuring, at a second time point, second location information for the subject using the first sensor, wherein a line of sight between the second sensor and the subject at the second time point is obscured; and
   determining whether a collision is expected to occur between the subject and the radiotherapy device based on the spatial profile and the second location information.

2. A method according to clause 1, comprising determining that a collision is expected to occur between the subject and the radiotherapy device based on the spatial profile and the second location information.

3. A method according to clause 2, comprising, in response to determining that the collision is expected to occur, halting movement of one or more components of the radiotherapy device.

4. A method according to clause 2 or clause 3, comprising, in response to determining that the collision is expected to occur, adjusting a speed of rotation and/or an angle of rotation of one or more components of the radiotherapy device.

5. A method according to any of clauses 2-4, comprising, in response to determining that the collision is expected to occur, adjusting a speed of translation and/or a translational position of one or more components of the radiotherapy device.

6. A method according to any preceding clause, wherein the first sensor comprises an end sensor disposed longitudinally spaced apart from the radiotherapy device and directed towards the radiotherapy device.

7. A method according to any preceding clause, wherein the second sensor comprises a side sensor disposed laterally relative to the radiotherapy device and directed towards the radiotherapy device.

8. A method according to any preceding clause, further comprising measuring the first location information and/or the second location information using a third sensor, wherein the third sensor is a further side sensor disposed laterally relative to the radiotherapy device and directed towards the radiotherapy device.

9. A method according to any preceding clause, wherein at least one of the first sensor, the second sensor, and the third sensor comprises a camera.

10. A method according to any preceding clause, further comprising generating a three-dimensional model of the radiotherapy device and the subject.

11. A method according to clause 10, further comprising determining, from the obscured line of sight between the second sensor and the subject at the second time point, a location of a component of the radiotherapy device obscuring the line of sight, and updating the three-dimensional model based on the location of the component.

12. An apparatus for use with a radiotherapy device, the apparatus comprising:

a first sensor configured to measure first location information for a subject at a first time point; and
a second sensor configured to measure first location information for the subject at the first time point,
wherein the first sensor is further configured to measure second location information for the subject at a second time point at which a line of sight between the second sensor and the subject is obscured,
the apparatus further comprising a controller configured to:
determine a spatial profile of the subject based on the first location information; and
determine whether a collision is expected to occur between the subject and the radiotherapy device based on the spatial profile and the second location information.

13. An apparatus according to clause 12, wherein the controller is configured to determine that a collision is expected to occur between the subject and the radiotherapy device based on the spatial profile and the second location information.

14. An apparatus according to clause 13, wherein the controller is configured to instruct that one or more components of the radiotherapy device be halted in response to determining that the collision is expected to occur.

15. An apparatus according to clause 13 or clause 14, wherein the controller is configured to instruct that a speed of rotation and/or an angle of rotation of one or more components of the radiotherapy device be adjusted in response to determining that the collision is expected to occur.

16. An apparatus according to any of clauses 12-15, wherein the controller is configured to instruct that a speed of translation and/or a translational position of one or more components of the radiotherapy device be adjusted in response to determining that the collision is expected to occur.

17. An apparatus according to any of clauses 12-16, wherein the first sensor comprises an end sensor configured to be disposed longitudinally spaced apart from the radiotherapy device and directed towards the radiotherapy device.

18. An apparatus according to any of clauses 12-17, wherein the second sensor comprises a side sensor configured to be disposed laterally relative to the radiotherapy device and directed towards the radiotherapy device.

19. An apparatus according to any of clauses 12-18, comprising a third sensor, wherein the third sensor is a further side sensor configured to be disposed laterally relative to the radiotherapy device and directed towards the radiotherapy device.

20. An apparatus according to any of clauses 12-19, wherein at least one of the first sensor, the second sensor, and the third sensor comprises a camera.

21. An apparatus according to any of clauses 12-20, wherein the controller is configured to generate a three-dimensional model of the radiotherapy device and the subject.

22. An apparatus according to clause 21, wherein the controller is configured to determine, from the obscured line of sight between the second sensor and the subject at the second time point, a location of a component of the radiotherapy device obscuring the line of sight, and to update the three-dimensional model based on the location of the component.

23. A computer readable medium comprising computer executable instructions which, when executed by a processor, cause the processor to perform the method of any of clauses 1-11.

24. A radiotherapy device comprising the apparatus of any of clauses 12-22.

The invention claimed is:

1. A method for avoiding a collision between a subject and a radiotherapy device, the method comprising:
measuring, at a first time point, first location information for the subject using a first sensor and a second sensor;
determining a spatial profile of the subject based on the first location information;
measuring, at a second time point, second location information for the subject using the first sensor, wherein a line of sight between the second sensor and the subject at the second time point is obscured;
determining that a collision is expected to occur between the subject and the radiotherapy device based on the spatial profile and the second location information;
in response to determining that the collision is expected to occur, adjusting at least one of a speed of rotation of one or more components of the radiotherapy device such that motion of the one or more components proceeds at a different speed, or an angle of rotation of one or more of the one or more components of the radiotherapy device, and
measuring at least one of the first location information or the second location information using a third sensor, wherein the third sensor is a side sensor disposed laterally relative to the radiotherapy device and directed towards the radiotherapy device.

2. The method according to claim 1, further comprising:
in response to determining that the collision is expected to occur, halting movement of the one or more components of the radiotherapy device.

3. The method according to claim 1, further comprising:
in response to determining that the collision is expected to occur, adjusting at least one of a speed of translation or a translational position of the one or more components of the radiotherapy device.

4. The method according to claim 1, wherein the first sensor comprises an end sensor disposed longitudinally spaced apart from the radiotherapy device and directed towards the radiotherapy device.

5. The method according to claim 1, wherein the second sensor comprises a side sensor disposed laterally relative to the radiotherapy device and directed towards the radiotherapy device.

6. The method according to claim 1, wherein at least one of the first sensor, the second sensor, or the third sensor comprises a camera.

7. The method according to claim 1, further comprising:
generating a three-dimensional model of the radiotherapy device and the subject.

8. The method according to claim 7, further comprising:
determining, from the obscured line of sight between the second sensor and the subject at the second time point, a location of a component of the radiotherapy device obscuring the line of sight, and updating the three-dimensional model based on the location of the component.

9. An apparatus for use with a radiotherapy device, the apparatus comprising:
a first sensor configured to measure first location information for a subject at a first time point; and
a second sensor configured to measure first location information for the subject at the first time point,
wherein the first sensor is further configured to measure second location information for the subject at a second time point at which a line of sight between the second sensor and the subject is obscured, and wherein the apparatus further comprises a controller configured to:

determine a spatial profile of the subject based on the first location information;

determine that a collision is expected to occur between the subject and the radiotherapy device based on the spatial profile and the second location information, and in response to determining that the collision is expected to occur, instruct that at least one of: a speed of rotation of one or more components of the radiotherapy device be adjusted such that motion of the one or more components proceeds at a different speed, or that an angle of rotation of one or more of the one or more components of the radiotherapy device be adjusted, wherein at least one of the first location information or the second location information is measured using a third sensor of the apparatus, wherein the third sensor is a side sensor configured to be disposed laterally relative to the radiotherapy device and directed towards the radiotherapy device.

10. The apparatus according to claim 9, wherein the controller is further configured to:

instruct that the one or more components of the radiotherapy device be halted in response to determining that the collision is expected to occur.

11. The apparatus according to claim 9, wherein the controller is further configured to:

instruct that at least one of a speed of translation or a translational position of the one or more components of the radiotherapy device be adjusted in response to determining that the collision is expected to occur.

12. The apparatus according to claim 9, wherein the first sensor comprises an end sensor configured to be disposed longitudinally spaced apart from the radiotherapy device and directed towards the radiotherapy device.

13. The apparatus according to claim 9, wherein the second sensor comprises a side sensor configured to be disposed laterally relative to the radiotherapy device and directed towards the radiotherapy device.

14. The apparatus according to claim 9, wherein at least one of the first sensor, the second sensor, or the third sensor comprises a camera, and wherein the apparatus is included in the radiotherapy device.

15. The apparatus according to claim 9, wherein the controller is further configured to:

generate a three-dimensional model of the radiotherapy device and the subject.

16. The apparatus according to claim 15, wherein the controller is further configured to:

determine, from the obscured line of sight between the second sensor and the subject at the second time point, a location of a component of the radiotherapy device obscuring the line of sight, and to update the three-dimensional model based on the location of the component.

17. A non-transitory computer-readable medium comprising computer executable instructions which, when executed by a processor, cause the processor to execute operations, the operations comprising:

measuring, at a first time point, first location information for a subject using a first sensor and a second sensor;

determining a spatial profile of the subject based on the first location information;

measuring, at a second time point, second location information for the subject using the first sensor, wherein a line of sight between the second sensor and the subject at the second time point is obscured;

determining that a collision is expected to occur between the subject and a radiotherapy device based on the spatial profile and the second location information;

in response to determining that the collision is expected to occur, adjusting at least one of a speed of rotation of one or more components of the radiotherapy device such that motion of the one or more components proceeds at a different speed, or an angle of rotation of one or more of the one or more components of the radiotherapy device, and measuring at least one of the first location information or the second location information using a third sensor wherein the third sensor is a side sensor disposed laterally relative to the radiotherapy device and directed towards the radiotherapy device.

18. The non-transitory computer-readable medium of claim 17, the operations further comprising:

in response to determining that the collision is expected to occur, halting movement of the one or more components of the radiotherapy device.

* * * * *